United States Patent
Ahn et al.

(10) Patent No.: US 9,429,525 B2
(45) Date of Patent: Aug. 30, 2016

(54) OPTICAL MODULE FOR SURFACE INSPECTION AND SURFACE INSPECTION APPARATUS INCLUDING THE SAME

(71) Applicant: SAMSUNG ELECTRONICS CO., LTD., Suwon-Si, Gyeonggi-Do (KR)

(72) Inventors: Myoung-Ki Ahn, Yongin-Si (KR); Jin-Woo Ahn, Suwon-Si (KR); Young-Gwon Kim, Seongnam-Si (KR); Tae-Jun Ahn, Seongnam-Si (KR); Tae-Yong Jo, Seoul (KR); Young Heo, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 0 days.

(21) Appl. No.: 14/791,607

(22) Filed: Jul. 6, 2015

(65) Prior Publication Data

US 2016/0047752 A1 Feb. 18, 2016

(30) Foreign Application Priority Data

Aug. 13, 2014 (KR) ........................ 10-2014-0105121

(51) Int. Cl.
*G01J 4/00* (2006.01)
*G01N 21/88* (2006.01)
*G01N 21/95* (2006.01)

(52) U.S. Cl.
CPC ...... *G01N 21/8806* (2013.01); *G01N 21/9501* (2013.01); *G01N 2021/8822* (2013.01); *G01N 2021/8848* (2013.01); *G01N 2201/062* (2013.01); *G01N 2201/0683* (2013.01)

(58) Field of Classification Search
CPC .............. G01J 4/00; G01N 21/8806; G01N 2021/8848; G01N 2021/8822; G01N 21/9501
USPC ............................................. 356/364
See application file for complete search history.

(56) References Cited

U.S. PATENT DOCUMENTS

| | | | |
|---|---|---|---|
| 6,608,676 B1 | 8/2003 | Zhao et al. | |
| 6,867,424 B2 | 3/2005 | Kurosawa et al. | |
| 7,271,889 B2 * | 9/2007 | Cemic ................ | G01N 21/8806 356/237.2 |
| 7,365,834 B2 * | 4/2008 | Lewis ................. | G01N 21/474 356/237.2 |
| 7,460,219 B2 | 12/2008 | Jung et al. | |
| 7,602,481 B2 | 10/2009 | Kreh | |
| 8,681,215 B2 | 3/2014 | King et al. | |

FOREIGN PATENT DOCUMENTS

| | | |
|---|---|---|
| JP | 2000-162134 | 6/2000 |
| JP | 2007-327896 | 12/2007 |

* cited by examiner

*Primary Examiner* — Roy M Punnoose
(74) *Attorney, Agent, or Firm* — Volentine & Whitt, PLLC

(57) ABSTRACT

An optical module for surface inspection includes a first light source unit that illuminates a substrate with first light produced by a first light source and a first beam splitter that changes the path of the first light, a second light source unit that illuminates the substrate with second light polarized in a first direction, a direction of polarization changing unit that illuminates the substrate with the third light polarized in a second direction perpendicular to the first direction, and a detection unit that detects fourth light which is a product of the first light reflecting from the substrate, fifth light which is a product of the second light scattered from the substrate, and sixth light which is a product of the third light scattered from the substrate. The third light is produced by changing the direction of polarization of the second light reflected from the inspected substrate.

20 Claims, 12 Drawing Sheets

OPTICAL MODULE FOR SURFACE INSPECTION AND SURFACE INSPECTION APPARATUS INCLUDING THE SAME

PRIORITY STATEMENT

This application claims priority from Korean Patent Application No. 10-2014-0105121 filed on Aug. 13, 2014 in the Korean Intellectual Property Office, and all the benefits accruing therefrom under 35 U.S.C. 119, the contents of which are hereby incorporated by reference in their entirety.

BACKGROUND

The present inventive concept relates to an optical module for surface inspection and a surface inspection apparatus including the same. More particularly, the inventive concept relates to an optical module for bright-field and dark-field surface inspection and a surface inspection apparatus including the same.

Recently, the manufacturing of semiconductor devices and displays has been carried out through the use of many discrete processes. Because defects in an intermediate product can impact any of these processes or any of these processes can give rise to manufacturing defects, defects are gradually becoming more and more likely to affect the precision of these products, their reliability and the production yield.

Therefore, it is becoming more and more important to detect defects in substrates used to manufacture semiconductor devices and displays and/or to precisely detect defects produced during a manufacturing process. In particular, inspection devices and methods must be able to detect a wide variety of defects.

SUMMARY

According to an aspect of the present inventive concept, there is provided an optical module for surface inspection comprising a first light source unit including a first light source that produces a first light and a first beam splitter that changes the direction along which the first light propagates from the first light source, a second light source unit that produces a second light polarized in a first direction, a direction of polarization changing unit, and a detection unit. The first light source unit is oriented to illuminate an imaging plane, corresponding to a surface of a substrate to be inspected using the module, with the first light whose direction of propagation has been changed by the beam splitter. The second light source is oriented to illuminate the imaging plane with the second light. The direction of polarization changing unit is oriented to receive the second light reflected from the imaging plane when the imaging plane is occupied by the surface of the substrate to be inspected. To that end the direction of polarization changing unit comprises optics which convert the second light received into third light polarized in a second direction, perpendicular to the first direction, and propagating in a direction back to the imaging plane. The detection unit is operative to detect captured light and positioned in the module to capture fourth light that is a product of the first light reflecting from the imaging plane, fifth light that is a product of the second light scattered from the imaging plane, and sixth light that is a product of the third light scattered from the imaging plane, all when the imaging plane is occupied by the surface of the substrate to be inspected.

According to another aspect of the present inventive concept, there is provided an optical module for surface inspection comprising a first light source unit configured to irradiate first light to an inspected substrate and including a first light source generating the first light and a first dichroic beam splitter changing a path of the first light, a second light source unit configured to irradiate second light to the inspected substrate, and a detection unit configured to detect third light generated by reflecting the first light on the inspected substrate and fourth light generated by scattering the second light on the inspected substrate. The third light and the fourth light pass through the first dichroic beam splitter to reach the detection unit, and the transmittance of the first dichroic beam splitter for the third light is 50%, and the transmittance of the first dichroic beam splitter for the fourth light is 90% or more.

According to still another aspect of the present inventive concept, there is provided an optical module for surface inspection comprising a first light source unit that outputs first light along a first optical axis of the module and includes a first light source, and a beam splitter oriented to reflect light produced by the first light source along the first optical axis of the module, a second light source unit that outputs light polarized in a first direction along a second optical axis that intersects the first optical axis at an imaging plane and is oblique with respect to the first optical axis, and a detection unit including a light detector, and in which the beam splitter is disposed along the first optical axis between the imaging plane and the light detector, and the beam splitter has a transmittance with respect to the first light and the polarized second light. Thus, the light detector captures light that is a product of the first light reflecting from a surface of a substrate oriented substantially perpendicular to the first optical axis and lying in the imaging plane, and captures light that is a product of the polarized second light scattered from the surface of the substrate.

BRIEF DESCRIPTION OF THE DRAWINGS

The above and other features and advantages of the present inventive concept will become more apparent by referring to the detailed description of preferred embodiments that follows as made with reference to the attached drawings in which.

DETAILED DESCRIPTION OF THE PREFERRED EMBODIMENTS

Figure 1:
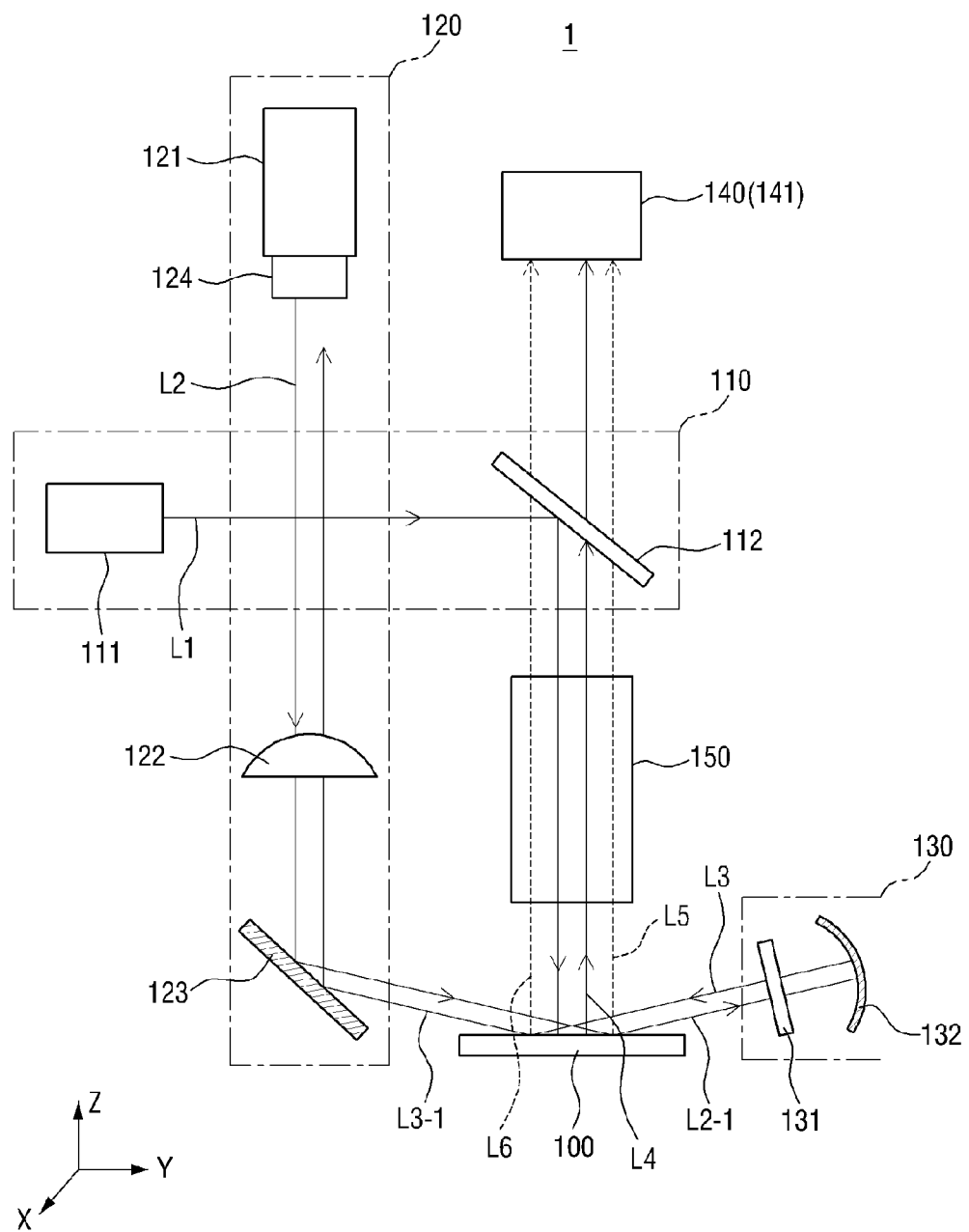
FIG. 1 is a schematic diagram of a first embodiment of an optical module for surface inspection according to the present inventive concept.

Advantages and features of the present inventive concept and methods of accomplishing the same may be understood more readily by reference to the following detailed description of preferred embodiments and the accompanying drawings. The present inventive concept may, however, be embodied in many different forms and should not be construed as being limited to the embodiments set forth herein. Rather, these embodiments are provided so that this disclosure will be thorough and complete and will fully convey the concept of the inventive concept to those skilled in the art, and the present inventive concept will only be defined by the appended claims. Like reference numerals refer to like elements throughout the specification.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present inventive concept.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present inventive concept.

Unless otherwise defined, all terms (including technical and scientific terms) used herein have the same meaning as commonly understood by one of ordinary skill in the art to which the present inventive concept belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Embodiments of the inventive concept will now be described in detail. In the figures, various optical axes of modules for surface inspection are shown in an idealized way by the arrows. Note, an optical axis between any two components may not necessarily be straight but, through the use of an optical component(s) along that optical axis may bend. Also, the surface of a substrate shown in each of the figures is also representative of an imaging plane of the modules. That is, as will be clear, in operation the substrate is supported and positioned such that its surface to be inspected coincides with the imaging plane of the module.

Hereinafter, a first embodiment of an optical module for surface inspection according to the present inventive concept will be described with reference to FIGS. 1 to 3B.

The optical module 1 includes a first light source unit 110, a second light source unit 120, a direction of polarization changing unit 130, a detection unit 140, and an objective lens 150.

The first light source unit 110 may illuminate a substrate 100 to be inspected with light L1. The first light source unit 110 may include a first light source 111 and a first beam splitter 112.

The first light source 111 produces a first beam of light, referred to hereinafter as the "light L1". The first light source 111 may be any of various kinds of light sources that produce light. For example, the first light source 111 may be a lamp comprising a light emitting diode (LED), a tungsten halogen lamp, or a xenon lamp.

The light L1 produced by the first light source 111 may be of any color. However, for convenience, the first light source 111 will be described as a source of white light.

The first beam splitter 112 changes the path along which the light L1 emanating from the first light source 111 propagates. The first beam splitter 112 is oriented to direct light received from the first light source 111 along a path to a surface of the substrate 100 to be inspected. These paths are thus part of an optical axis of the module.

More specifically, the first beam splitter 112 reflects some of the light L1 and transmits the rest of the light L1 therethrough (along a path not shown in the figure). For example, the first beam splitter 112 may reflect 50% of the light L1 produced by the first light source 111 and transmit 50% of the light L1. That is, 50% of the light L1 produced by the first light source 111 may be reflected by the first beam splitter 112 to illuminate the substrate 100 to be inspected.

Note, however, the reflection and transmission of incident light by the first beam splitter 112 is described in an idealized way. That is, although 50% of the light L1 produced by the first light source 111 is described as being transmitted and the rest reflected by the beam splitter, such a description is not intended to limit the embodiment to performing in this particular way. For instance, some of the light L1 may be absorbed by the first beam splitter 112 and in this case, the ratio of reflected light to incident light may be less than 50%.

In any case, the light L1 reflected by the first beam splitter 112 passes through the objective lens 150 to the substrate 100 to be inspected. Note, a lens may also be disposed along the optical axis between the first light source 111 and the first beam splitter 112 so as to collect the light L1 from the first light source 111 and focus the light on the beam splitter 112. However, such a lens is optional.

The substrate 100 to be inspected may be, for example, a rigid substrate such as a silicon substrate, a silicon-germanium substrate, a silicon-on-insulator (SOI) substrate, a gallium-arsenide substrate, and a glass substrate for a display or may be a flexible substrate. Furthermore, the substrate 100 may have a pattern formed on its surface to be illuminated by the light L1 or its surface to be illuminated may be substantially flat.

The light L1 produced by the first light source unit 110 is used to create a bright-field image of the substrate 100.

The second light source unit 120 illuminates the surface of the substrate 100 to be inspected with a second beam of light, referred to hereinafter as "light L2". The light L2 is polarized in one direction. That is, the light L2 is linearly polarized.

The second light source unit 120 may include a second light source 121 that produces the light L2, and a first lens 122. The second light source 121 may be a laser. For example, the second light source 121 may be a HeNe laser, an Ar laser, or a laser diode (LD).

The second light source 121 may produce the light as linearly polarized in a given direction X. Alternatively, in the case in which the second light source 121 is not oriented such that the light produced is polarized in the direction X, the second light source unit 120 may have an optical isolator 124, e.g., a Faraday isolator, to output only the light L2 that is polarized in the direction X.

FIG. 1 shows an example in which the optical isolator 124 is connected directly the second light source 121, but the optical isolator 124 may be spaced along an optical axis of the second light source unit 120 from the second light source 121.

For reference and illustration purposes, the plane containing the light L2 that is input to, i.e., illuminates the substrate 100 to be inspected, and is output from (reflected by) the light L2 is the Y-Z plane in the figures.

Thus, for s-polarized light L2, the direction of polarization would be the first direction X, i.e., normal to the Y-Z plane. For p-polarized light L2, the direction of polarization would be a direction parallel to the Y-Z plane, e.g., second direction Y or a third direction A that is any direction perpendicular to direction X. In any case, light polarized in the first direction X, e.g., the s-polarized light L2 in this example, does not pass through the first beam splitter 112 of the first light source unit 110.

Note, this example is one in which the light L2 produced by the second light source unit 120 is polarized in a direction corresponding to the direction of s-polarized light, but the inventive concept is not so limited. That is, the embodiment may be configured such that the light L2 is polarized in a direction corresponding to p-polarized light.

The first lens 122 focuses the light L2 polarized in the first direction X into the form a line. That is, the beam of light L2 transmitted by the first lens 122 may have a rectangular cross section (i.e., a rectangular form in the X-Z plane).

To this end, the first lens 122 may be a cylindrical lens, but other types of lenses may be used instead.

The second light source unit 120 may have a first minor 123 disposed along an optical axis between the first lens 122 and the substrate 100 to be inspected to reflect light from the first lens 122 onto the surface of the substrate to be inspected. The first minor 123 is provided in a case in which the optical axis of the second light source 121 is not oblique to the surface of the substrate 100 to be inspected. Otherwise, the first minor 123 may be omitted.

In any case, the light L2 produced by the second light source unit 120 and irradiating the surface of the substrate 100 to be inspected is used to create a dark-field image of the substrate 100.

The direction of polarization changing unit 130 produces a beam of light, referred to hereinafter as "light L3", polarized in a direction B which is parallel to the Y-Z (plane in which the light L2 polarized in the first direction X is input to the substrate 100 to be inspected). Here, direction B may be any direction which is perpendicular to the first direction X, namely the direction of polarization of the light L2 incident on the substrate 100 as well as the direction of polarization of the light L2_1 reflected from the substrate 100 as a result along a different direction of propagation. Also, as is shown best in FIG. 3b, the direction B is perpendicular to the direction propagation of the light L3 and to the first direction X.

The light L3 is produced by changing the direction of polarization of the light L2_1 reflected by the substrate 100 to be inspected.

To this end, the direction of polarization changing unit 130 may include a quarter wave plate 131 and a second mirror 132.

The process by which the reflected light L2-1, which is polarized in the first direction X, is converted into the light L3 polarized in the direction B will be described with reference to FIG. 2.

Figure 2A:
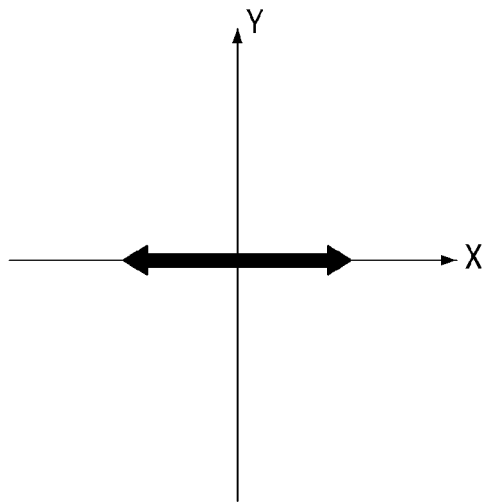
FIGS. 2A, 2B, 2C and 2D are conceptual diagrams illustrating changes in direction of polarization of light passing through a direction of polarization changing unit of the module of FIG. 1.

FIG. 2A shows the light L2_1 reflected by the substrate 100 as linearly polarized in the first direction X.

Figure 2B:
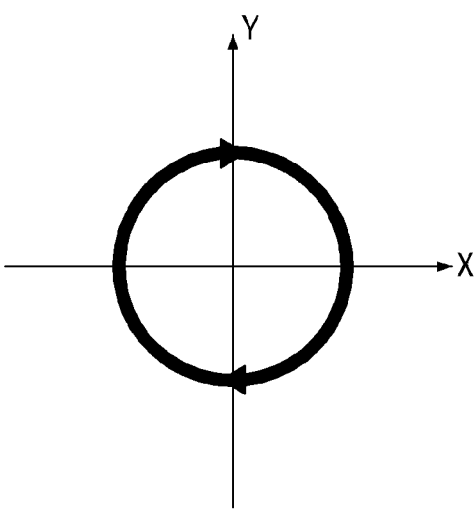

Subsequently, as illustrated in FIG. 2B, the light L2_1 passes through the quarter wave plate 131 and as a result, is converted into light that has circular polarization. In particular, a characteristic matrix of the quarter wave plate 131, namely, an optical property of the material of the quarter wave plate 131, converts the light L2_1 from linearly-polarized light to circularly-polarized light.

Subsequently, the circularly-polarized light L2_1 is reflected by the second mirror 132 back to the quarter wave plate 131. The second minor 132 may be a concave mirror, but other types of reflectors may be used instead.

In the example of FIG. 1, the polarization direction changing unit 130 does not include any other optical component besides the second minor 132 and the quarter wave plate 131, but this is just for convenience of the description and the present embodiment is not limited to such a polarization direction changing unit 130.

For example, if the second minor 132 is not a concave minor, another optical component(s) (for example, a lens or the like) is/are additionally disposed between the second minor 132 and the quarter wave plate 131 to direct the circularly-polarized light back to the quarter wave plate 131.

Figure 2C:
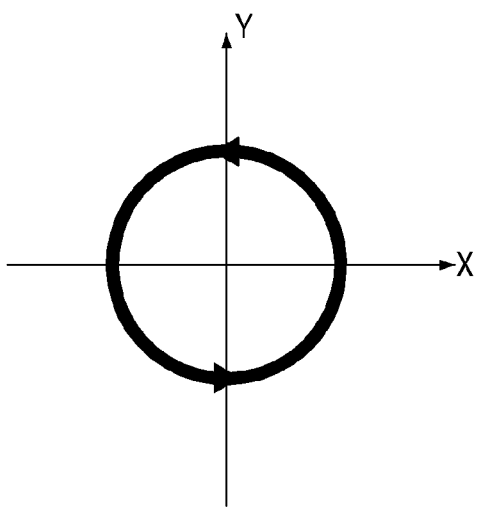
Figure 2D:
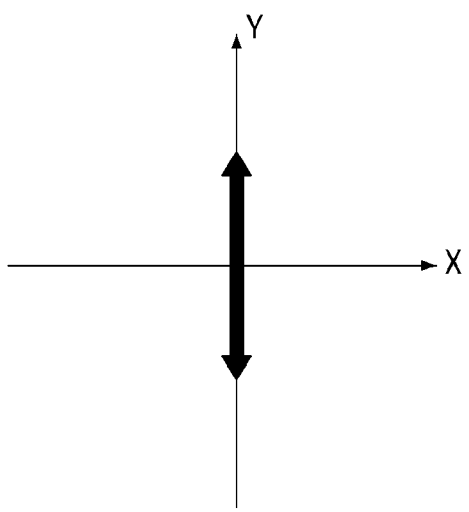
Figure 3A:
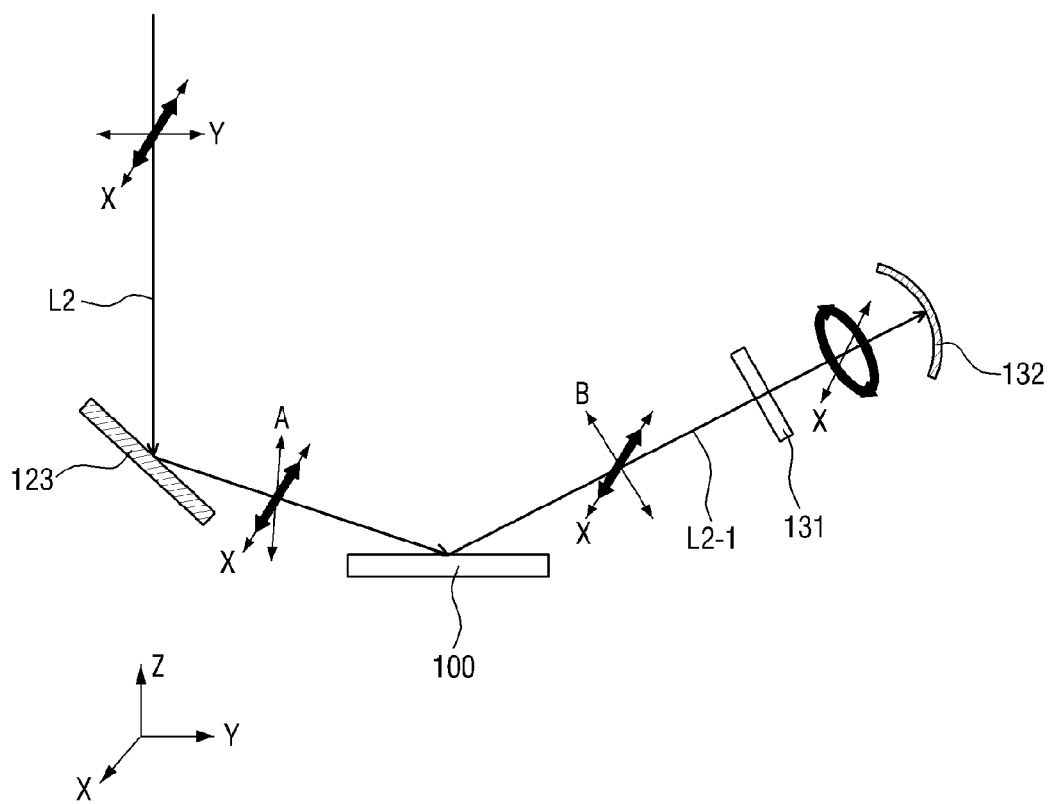
FIG. 3A is a schematic diagram illustrating a relationship between a direction of propagation and a direction of polarization of second light in the operation of the module of FIG. 1.
Figure 3B:
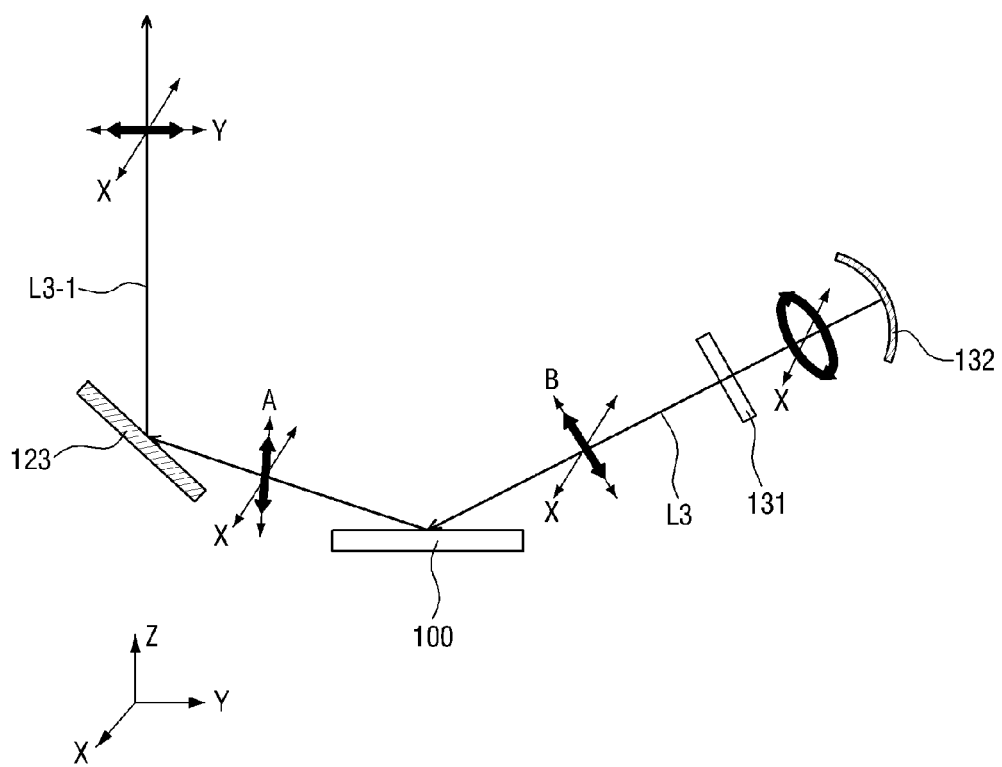
FIG. 3B is a schematic diagram illustrating a relationship between a direction of propagation and a direction of polarization of third light in the operation of the module of FIG. 1.

The circularly-polarized light which is incident on the quarter wave plate 131 passes through the quarter wave plate 131, and is thereby converted into the linearly-polarized light L3 as illustrated in FIG. 2C.

In other words, the light L2 which is linearly polarized in the first direction X passes through the quarter wave plate 131 twice, thereby being converted to the light L3 linearly polarized in a direction B perpendicular to the first direction X.

The light L3 incident on the substrate 100 to be inspected may be reflected from the substrate 100 toward the second light source 121 through the first minor 123 and the first lens 122 as light L3_1. Even though light L3_1 may head for the second light source 121, in this example, the light L3_1 is prevented from entering the second light source 121 by the optical isolator 124.

The light L3, having been twice polarized by the direction of polarization changing unit 130 and irradiating to the substrate 100 to be inspected, is used to create the dark-field image of the substrate.

Furthermore, note that FIG. 1 shows the light L1, the light L2, and the light L3 impinging the substrate 100 to be inspected at different location, but this is just for ease of illustration. That is, the light L1, the light L2, and the light L3 illuminate the same area of the surface of the substrate 100.

The detection unit 140 detects rays of light which are reflected or scattered from the substrate 100. The rays of light include those of the light L1 reflecting from the substrate 100 (referred to hereinafter as "light L4"), those of the light L2 scattered from the substrate 100 (referred to hereinafter as "light L5"), and those of the light L3 scattered from the substrate 100 (referred to hereinafter as "light L6").

Because the light L5 is the product of the light L2 scattered from the substrate 100, the light L5 is polarized in the first direction X. For similar reasons, the light L6 may be polarized in the second direction Y.

The light L4, the light L5, and the light L6 pass through the objective lens 150 and are incident on the first beam splitter 112. As a result, part of each of the fourth light L4, the light L5, and the light L6 is transmitted by the beam splitter 112 to the detection unit 140 and a part thereof is reflected. For example, 50% of each of the light L4, the light L5, and the light L6 may be transmitted, and 50% of each of the light L4, the light L5, and the light L6 may be reflected.

The detection unit 140 includes a first detector 141. In the example in which the light L2 and the light L3 are shaped, as the result of having passed through lens 122, so as have an elongated (rectangular) cross section, the first detector 141 may be a line scan camera.

The first detector 141 detects the light L4 to create the bright-field image of the substrate 100 to be inspected. The first detector 141 detects the light L5 and the light L6 to create the dark-field image of the substrate 100.

Even though not illustrated in FIG. 1, the detection unit 140 may further include a lens disposed between the first detector 141 and the first beam splitter 112. The lens may serve to help the first detector 141 create the bright-field image and/or the dark-field image.

In the above-described embodiments of an optical module for surface inspection according to the present inventive concept, the light L4 used for creating the bright-field image and the light L5 and the light L6 used for creating the dark-field image pass through the same objective lens 150 and the first beam splitter 112. As a result, the optical module for surface inspection may be relatively compact or miniature.

Next, the effects of the direction of polarization changing unit 130 will be described in detail.

First, the second light source unit 120 illuminates the substrate 100 to be inspected with the light L2, and the direction of polarization changing unit 130 illuminates the substrate 100 to be inspected with the light L3. Therefore, the substrate 100 to be inspected is illuminated with a relatively large amount of light due to the provision of the direction of polarization changing unit 130. In other words, the direction of polarization changing unit 130 in effect increases the amount of the light used for creating the dark-field image of the substrate 100. Accordingly, an additional second light source 121 is unnecessary, i.e., the direction of polarization changing unit 130 allows for size and the cost savings in the optical module.

Likewise, the direction of polarization changing unit 130 allows the substrate 100 to be illuminated with light L2 and light L3 which are linearly polarized in different directions using only one light source, namely, the second light source 121.

When the substrate 100 to be inspected has a defect, images of the defect may vary depending on the direction of the light used to illuminate the substrate. That is, depending on a shape of the defect of the substrate 100, the defect may be sensitively detected by the light L2 polarized in the first direction X, or may be sensitively detected by the light L3 polarized in the direction B. Accordingly, a defect of the substrate 100 may be precisely identified and/or more assuredly detected by illuminating the substrate 100 with the light L2 and the light L3 having different directions of polarization as provided through the use of the polarization detection changing unit 130.

Other embodiments of optical modules for surface inspection will be described in detail below. For the sake of brevity, and because like reference numerals designate like elements throughout the figures, mainly only the differences between the embodiments will be described in detail.

Figure 4:
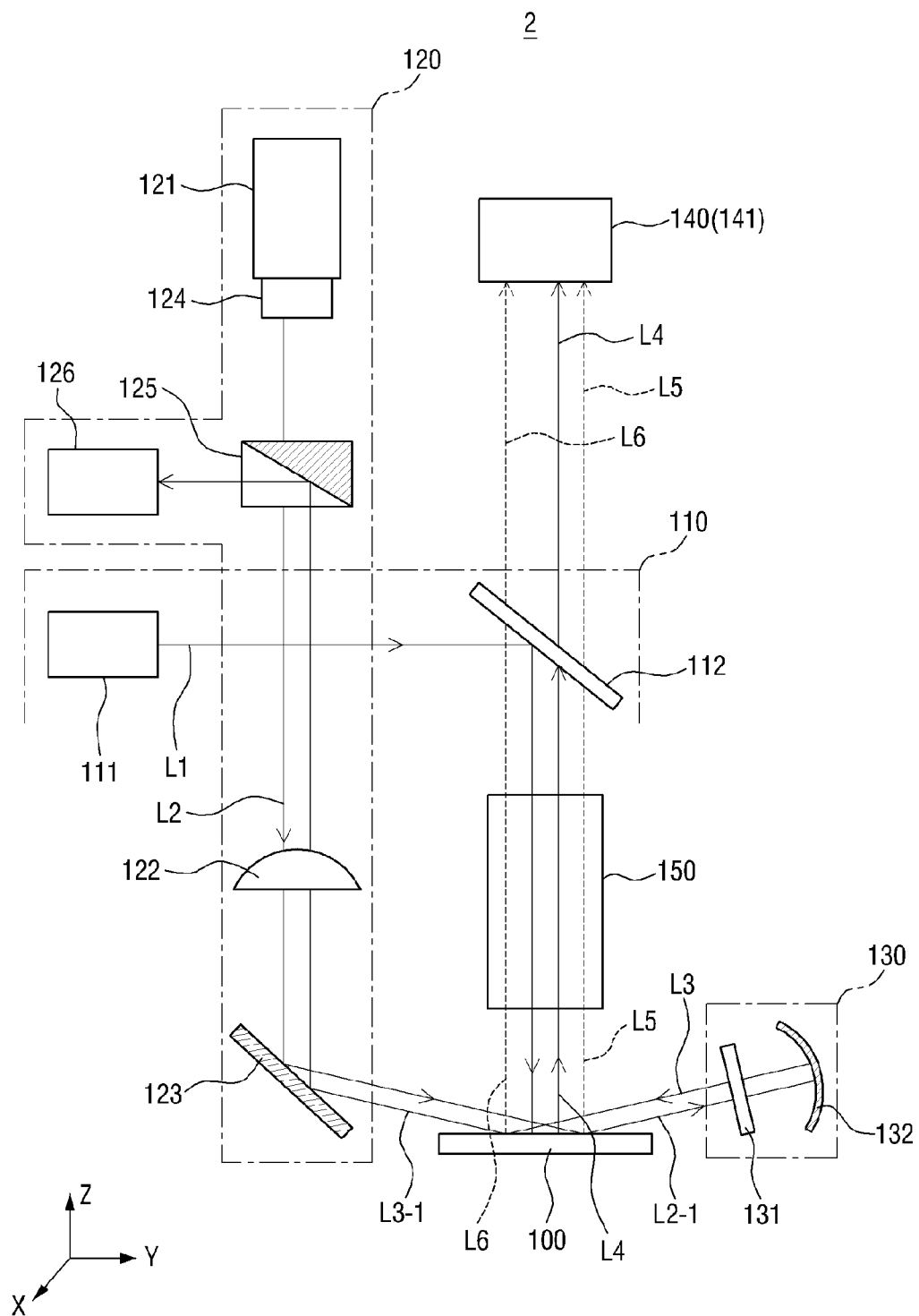
FIG. 4 is a schematic diagram of a second embodiment of an optical module for surface inspection according to the present inventive concept.

FIG. 4 illustrates a second embodiment of an optical module for surface inspection according to the present inventive concept.

Referring to FIG. 4, in the second embodiment of an optical module 2 for surface inspection according to the present inventive concept, the second light source unit 120 further includes a second beam splitter 125 and a beam dump 126.

The second beam splitter 125 may be disposed between the second light source 121 and the first lens 122. That is, the light L2 polarized in the first direction X may be transmitted to the first lens 122 through the second beam splitter 125.

The second beam splitter 125 may be a polarizing beam splitter. That is, the second beam splitter 125 may transmit or reflect incident light depending on the direction of polarization of the incident light.

For example, the second beam splitter 125 may transmit the light polarized in the first direction X and reflect the light polarized in the second direction Y. That is, the light L2 polarized in the first direction X may pass through the second beam splitter 125, but the light L3 polarized in the second direction Y does not pass through the second beam splitter 125, but is reflected in the second beam splitter 125.

The light L3_1 polarized in the second direction Y, and reflected from the substrate 100, is reflected by the first mirror 123 to the second beam splitter 125. Therefore, the light L3_1 is reflected by the second beam splitter 125 and does not reach the second light source 121. Accordingly, the second light source 121 is prevented from being damaged by the light L3_1.

Further, the second light source unit 120 may only illuminate the substrate 100 to be inspected with the light L2 polarized in the first direction X because light polarized only in the first direction X can pass through the second beam splitter 125.

The beam dump 126 may absorb the light L3_1 which does not pass through the second beam splitter 125 but is reflected. That is, the beam dump 126 may absorb the light L3_1 which is created by the direction of polarization changing unit 130 and then reflected by the substrate 100 to be inspected back to the second light source unit 120.

Figure 5:
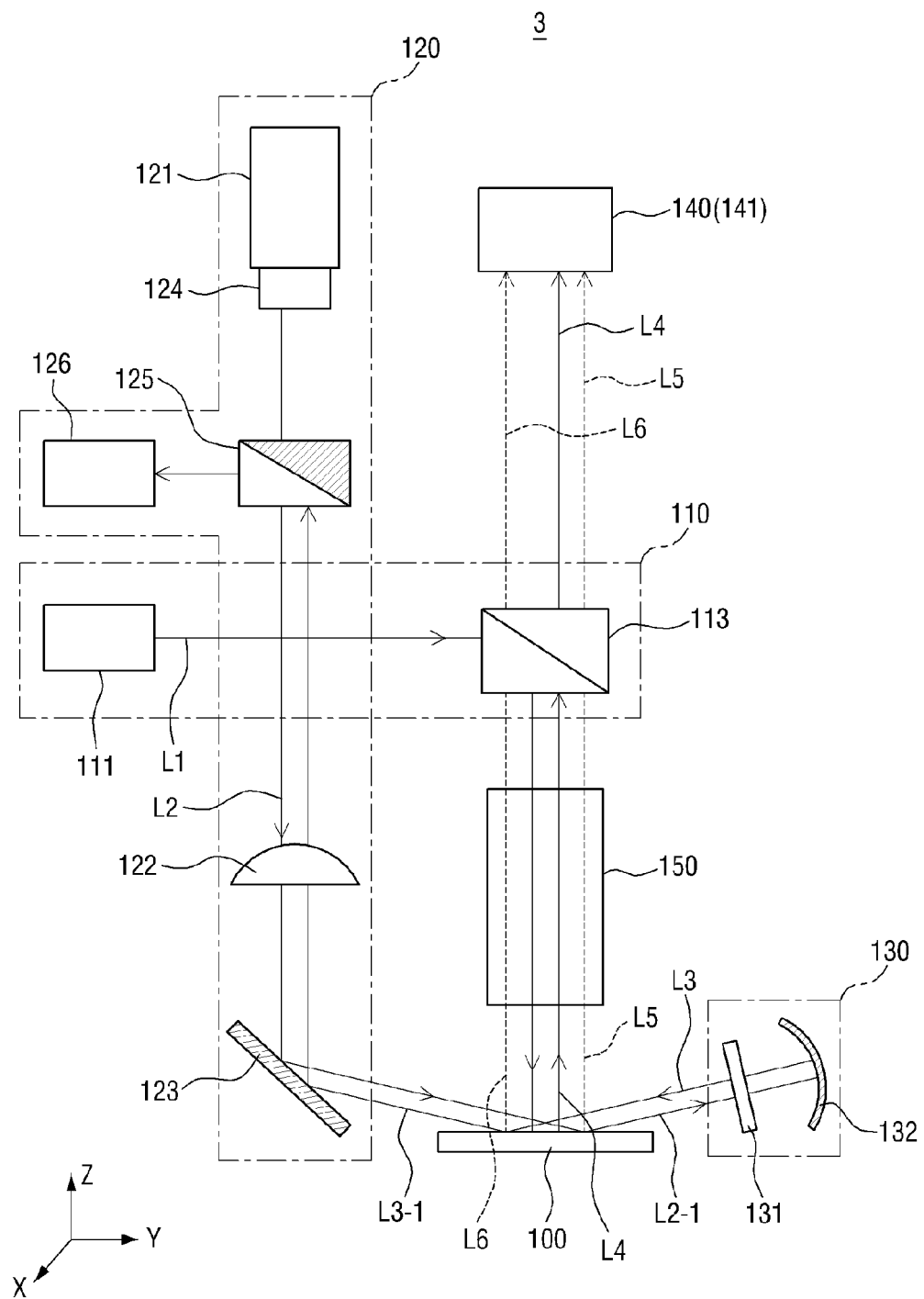
FIG. 5 is a schematic diagram of a third embodiment of an optical module for surface inspection according to the present inventive concept.

FIG. 5 illustrates a third embodiment of an optical module for surface inspection according to the present inventive concept.

Referring to FIG. 5, the third embodiment of an optical module 3 for surface inspection according to the present inventive concept employs a dichroic (mirrored prism) beam splitter 113 instead of the first beam splitter 112. That is, the transmittance of the dichroic beam splitter 113 varies depending on the wavelength of the incident light.

For example, the transmittance of the third dichroic splitter 113 for the light L1 and the light L4 is about 50%, and the transmittance of the third beam splitter 113 for the light L5 and the light L6 is 90% or more. That is, the dichroic beam splitter 113 may transmit 50% of the light used for making the bright-field image (i.e., light L4) and transmit most of the light used for making the dark-field image (i.e., the light L5 and the light L6).

This is because the light L4 is the produced from the light L1 and thus, the light L4 may have substantially the same wavelength spectrum as the light L1. Furthermore, the light L5 and the light L6 are produced by the light generated by the second light source 121 and thus, the light L5 and the light L6 may have substantially the same wavelength spectrum.

In addition, as described above, the first light source 111 may be a white light source, and the second light source 121 may be a laser light source. A white light source has a relatively wide wavelength band compared to a laser light source.

The dichroic beam splitter 113 may include a material (dichroic optical coating) which can transmit 90% or more of light having a wavelength corresponding to the wavelength of the second light source 121 and transmit only 50% of the light having the remaining wavelengths. As a result, the dichroic beam splitter 113 may transmit 50% of the light L4 and transmit most of the fifth light L5 and the sixth light L6.

Advantages of using the dichroic beam splitter 113 are as follows.

The light L4 used for making the bright-field image is the product of light reflected by the substrate 100 to be inspected. However, the light L5 and the light L6 used for making the dark-field image are the product of light scattered from the substrate 100. Therefore, the amount of light used for making the dark-field image (the light L5 and light L6) may be much smaller than the amount of the light used for making the bright-field image (the light L4).

Accordingly, the dichroic beam splitter 113 can maximize the amount of light L5 and light L6 which reach the first detector 141 to create the dark-field image. Therefore, the first detector 141 may create a very clear dark-field image.

Figure 6:
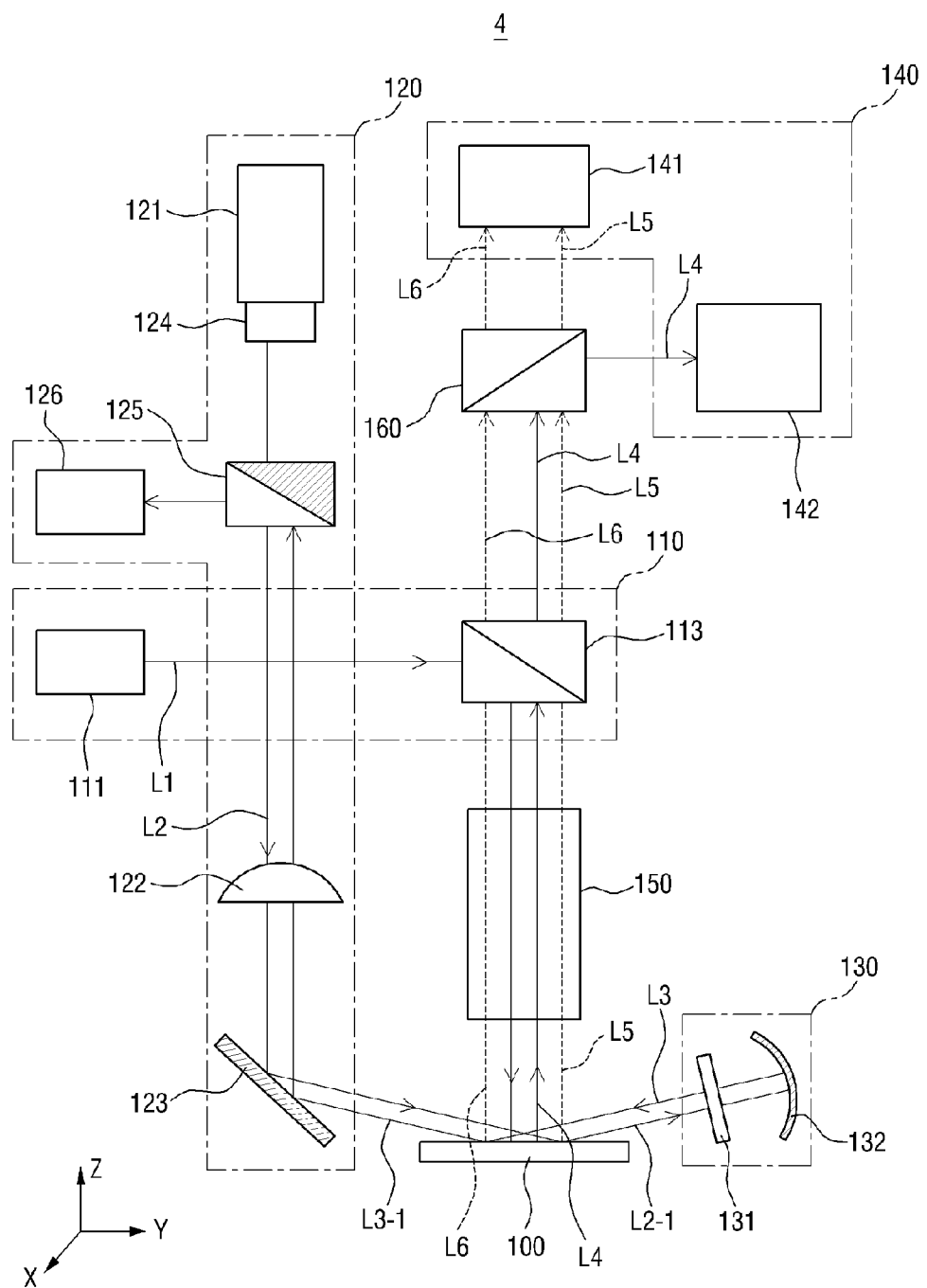
FIG. 6 is a schematic diagram of a fourth embodiment of an optical module for surface inspection according to the present inventive concept.

FIG. 6 illustrates a fourth embodiment of an optical module for surface inspection according to the present inventive concept.

Referring to FIG. 6, the fourth embodiment of an optical module 4 for surface inspection according to the present inventive concept may further include an additional beam splitter 160. Furthermore, the detection unit 140 may include a first detector 141 and a second detector 142.

The beam splitter 160 is disposed along the optical axis between the dichroic beam splitter 113 and the detection unit 140. That is, the portions of the light L4, L5, and L6 which pass through the dichroic beam splitter 113 pass into the detection unit 140 via the beam splitter 160.

The beam splitter 160 may be a dichroic beam splitter. The dichroic beam splitter 160 may transmit 90% or more of incident light having a predetermined wavelength band and reflect all the light having the remaining wavelengths.

For example, the transmittance of the beam splitter 160 to the light L5 and the light L6 derived from the second light source 121 which may be a laser light source is 90% or more, and the transmittance of the beam splitter 160 to the light L4 may be close to 0%. That is, almost 100% of the light L4 may be reflected by the fourth beam splitter 160.

The light L5 and the light L6 which pass through the beam splitter 160 may be detected by the first detector 141. On the contrary, the light L4 reflected by the fourth beam splitter 160 may be detected by the second detector 142.

In other words, in the optical module 4 for surface inspection according to the present inventive concept, the first detector 141 may create the dark-field image, and the second detector 142 may create the bright-field image. Accordingly, the dark-field image and the bright-field image may be simultaneously created.

In one example of the optical module 4 for surface inspection, the first light source 111 is a white light source and the second light source 121 is a laser light source generating laser light within the visible spectrum, the part of the spectrum that can be detected by the first detector 141 and the second detector 142 is the visible spectrum. The reason for this is that most of the energy of the white light source is distributed in the visible spectrum.

The smaller the wavelength of light used for surface inspection of the substrate 100, the greater is the ability to detect a surface defect by the light scattering produced by the defect. That is, in the case of using light having a small wavelength for surface inspection, the scattering of the light by any defect becomes more pronounced. As a result, the dark-field image is quite clear.

In another example of the optical module 4 for surface inspection, the first light source 111 is a white light source and the second light source 121 is a laser light source generating laser light within the ultraviolet spectrum, the part of the spectrum that can be detected by the first detector 141 is the ultraviolet spectrum and the part of the spectrum that can be detected by the second detector 142 may be the visible light spectrum.

Examples have been described in which the parts of the spectrum that can be detected by each of the first detector 141 and the second detector 142 correspond to the wavelength band of the light produced by the first light source 111 and the second light source 121, respectively, but the present embodiment is not limited to these examples. That is, a detector which can detect a wide range of wavelengths from those of the ultraviolet spectrum to those of the infrared spectrum with the same sensitivity can be used. That is each of the first detector 141 and the second detector 142 need not to be tailored to the wavelength band of the light produced by the first light source 111 and the second light source 121, respectively.

Figure 7:
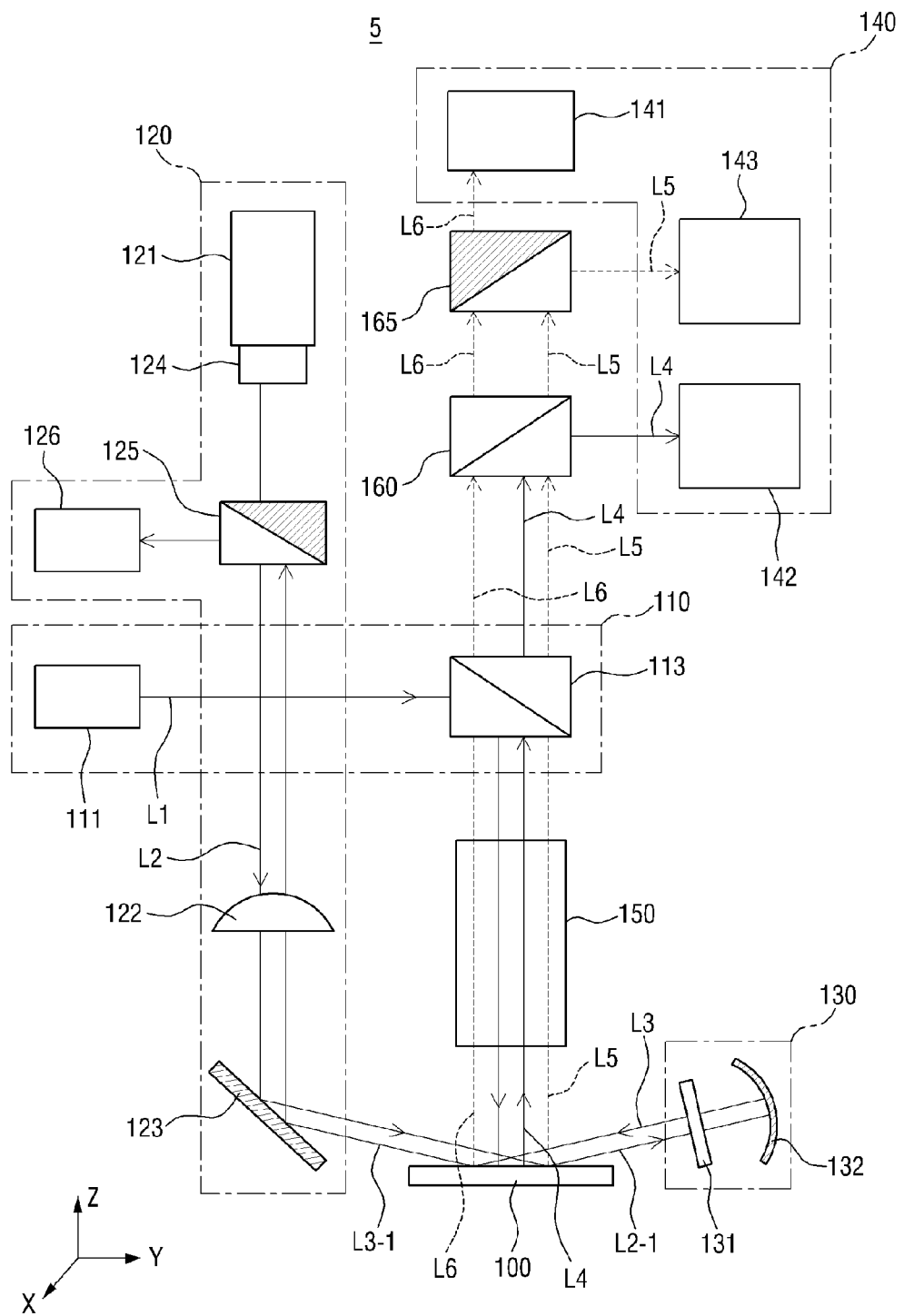
FIG. 7 is a schematic diagram of a fifth embodiment of an optical module for surface inspection according to the present inventive concept.

FIG. 7 is a schematic diagram for describing an optical module for surface inspection according to a fifth embodiment of the present inventive concept. For convenience of the description, differences from the description with reference to FIG. 6 will be mainly described.

FIG. 7 illustrates a fifth embodiment of an optical module 5 for surface inspection according to the present inventive concept. Optical module 5 includes a beam splitter 165. Furthermore, the detection unit 140 further includes a third detector 143.

In this embodiment, the light L5 and the light L6 which are transmitted through the beam splitter 160 are incident on the beam splitter 165. The beam splitter 165 is, for example, a polarizing beam splitter. Thus, the beam splitter 165 may transmit light polarized in a predetermined direction and reflect the rest of the light.

For example, the beam splitter 165 may reflect the light L5 and transmit the light L6. That is, the fifth beam splitter 165 may transmit light polarized in the second direction Y and reflect light polarized in the first direction X.

The light L6 which is transmitted by (passes through) the beam splitter 165 is detected by the first detector 141. On the contrary, the light L5 reflected by the beam splitter 165 is detected by the third detector 143.

The beam splitter 165 allows dark-field images to be produced by the light L5 and the light L6 polarized in the different directions. As a result, the surface of the substrate 100 to be inspected may be more precisely analyzed, i.e., such that the shape, size, and the like of the defect at the surface may be determined FIG. 8 illustrates a sixth embodiment of an optical module for surface inspection according to the present inventive concept.

Figure 8:
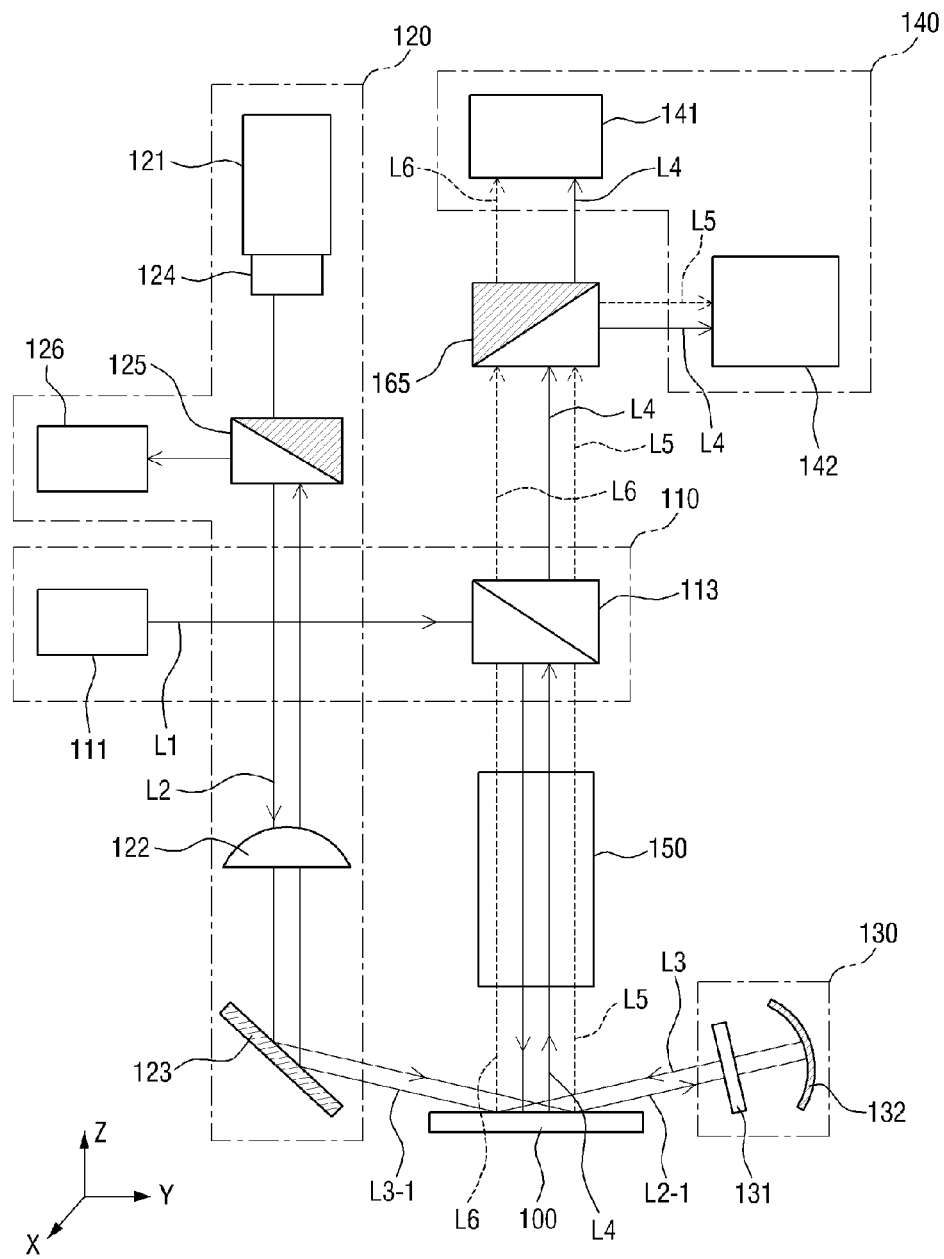
FIG. 8 is a schematic diagram of a sixth embodiment of an optical module for surface inspection according to the present inventive concept.

Referring to FIG. 8, optical module 6 for surface inspection includes a beam splitter 165. Furthermore, the detector 140 includes a first detector 141 and a second detector 142.

The beam splitter 165 is disposed along the optical axis between the beam splitter 113 and the detection unit 140. Therefore, the light L4, the light L5, and the light L6 which pass through the third beam splitter 113 are directed to the detectors 141 and 142 of the detection unit 140 by the beam splitter 160.

The beam splitter 165 is, for example, a polarizing beam splitter. That is, the beam splitter 165 may transmit light polarized in a predetermined direction and reflect the rest of the light. For example, the beam splitter 165 may transmit light polarized in the second direction Y and reflect light polarized in the first direction X.

Because the light L5 is the light polarized in the first direction X, the fifth beam splitter 165 reflects the light L5. Furthermore, because the light L4 is the light produced by the first light source 111, the fourth light L4 may be circularly polarized.

Accordingly, the beam splitter 165 reflects a component of the fourth light L4 polarized in the first direction X.

Because the light L6 is polarized in the second direction Y, the beam splitter 165 transmits the light L6. Furthermore, the beam splitter 165 reflects a component of the fourth light L4 polarized in the second direction Y.

That is, the beam splitter 165 reflects the light L5 and part of the light L4 and transmits the light L6 and another part of the light L4.

The light L5 and the part of the fourth light L4 reflected by the beam splitter 165 are detected by the second detector 142, and the light L6 and the other part of the light L4 transmitted by the beam splitter 165 are detected by the first detector 141.

Figure 9:
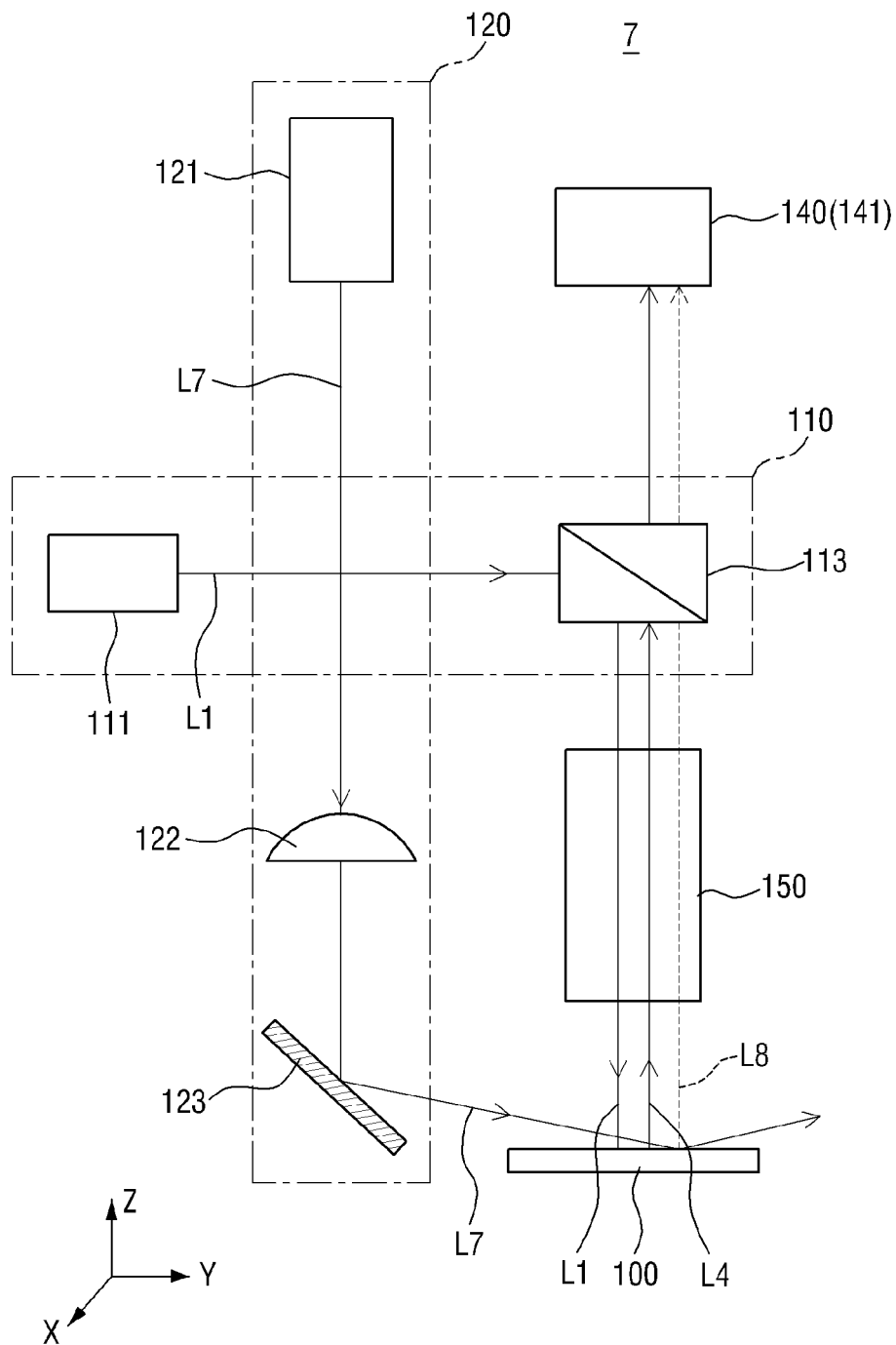
FIG. 9 is a schematic diagram of a seventh embodiment of an optical module for surface inspection according to the present inventive concept.

FIG. 9 illustrates a seventh embodiment of an optical module for surface inspection according to the present inventive concept. The optical module 7 is substantially the same as that of the embodiment described with reference to FIG. 5 except that it does not employ the direction of polarization changing unit 130, the beam splitter 125, the beam dump 126, and the optical isolator 124.

Therefore, referring to FIG. 9, the optical module 7 includes a first light source unit 110, a second light source unit 120, a detection unit 140, an objective lens 150, and the like.

The first light source unit 110 may illuminate a substrate 100 to be inspected with light Ll. The first light source unit 110 includes a first light source 111 and a dichroic beam splitter 113. The beam splitter 113 thus reflects some of the light L1 and transmits the rest of the light L1.

For example, the beam splitter 113 may reflect 50% of the light L1 produced by the first light source 111 and transmit 50% of the light L1 produced by the first light source 111.

The light L1 reflected by the beam splitter 113 passes through the objective lens 150 to illuminate the substrate 100 to be inspected.

The second light source unit 120 illuminates the substrate 100 to be inspected with light L7. The second light source unit 120 may include a second light source 121 and a first lens 122.

The light L7 produced by the second light source 121 may be shaped by the first lens 122 into a beam having an elongated cross section, e.g., a rectangular cross section, perpendicular to its direction of propagation.

The transmittance of the dichroic splitter 113 to the light L7 may be 90% or more. However, the seventh light L7 that passes through the dichroic beam splitter 113 does not illuminate the substrate 100 to be inspected.

The detection unit 140 detects light L4 and light L8 which are reflected or scattered from the substrate 100. The light L4 is the product of light L1 reflected from the substrate 100, and the light L8 is the product of light L7 scattered from the substrate 100.

The light L4 and the light L8 pass through the objective lens 150 and the dichroic beam splitter 113, before being detected by the detection unit 140.

In the optical module 7 for surface inspection according to the present inventive concept, the transmittance of the dichroic beam splitter 113 to the light L4 may be about 50%, and the transmittance of the dichroic beam splitter 113 to the light L8 may be 90% or more.

That is, the dichroic beam splitter 113 may transmit 50% of the light L4 used for creating the bright-field image and transmit most of the light L8 used for creating the dark-field image.

Figure 10:
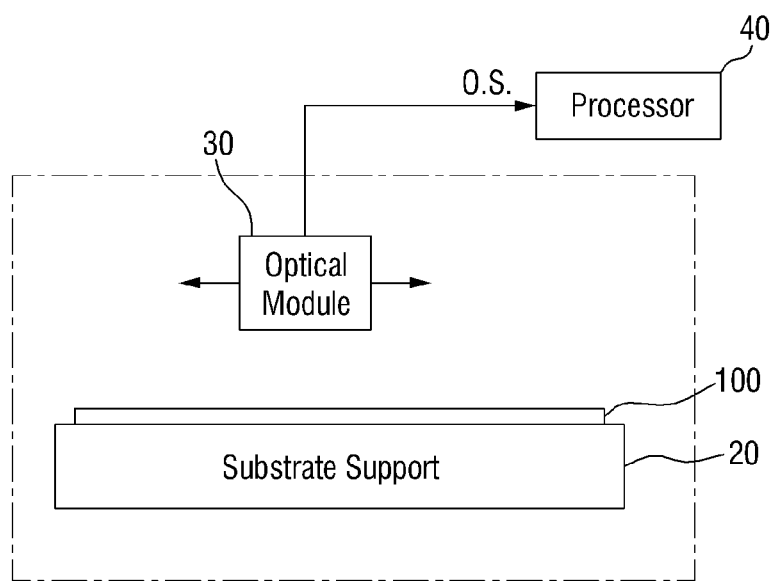
FIG. 10 is a block diagram of a surface inspection apparatus according to the present inventive concept.

FIG. 10 illustrates a surface inspection apparatus according to the present inventive concept.

Referring to FIG. 10, a surface inspection apparatus 8 includes a substrate support 20, and an optical module 30 for surface inspection.

The substrate support 20 may include a stage on which the substrate 100 to be inspected is disposed. The substrate support 20 may include a drive mechanism for moving the stage. The substrate 100 to be inspected may be fixed to the substrate support 20. Thus, the stage may comprise a chuck.

The optical module 30 for surface inspection is disposed above the substrate 100 as supported by the substrate support 20. The optical module 30 for surface inspection may comprise one or more discrete sets of optical components.

In order for the entirety of the substrate 100 to be inspected, the substrate support 20 and the optical module 30 for surface inspection may move relative to one another. For example, as mentioned above, a driving mechanism may drive a stage of the substrate support. The optical module 30 for surface inspection may output an optical signal O.S. from the substrate 100 to be inspected while the substrate 100 and the optical module 30 move relatively to each other.

The optical module 30 for surface inspection is any one of the optical modules described with reference to FIGS. 1 to 9.

The optical signal O.S. is thus a signal output by the detection unit 140 of the optical module 30 and is input to the processor 40. A surface state of the substrate 100 to be inspected, that is, whether a defect exists at the surface of the substrate 100, may be determined by the processor 40 using the optical signal O.S.

Finally, embodiments of the inventive concept and examples thereof have been described above in detail. The inventive concept may, however, be embodied in many different forms and should not be construed as being limited to the embodiments described above. Rather, these embodiments were described so that this disclosure is thorough and complete, and fully conveys the inventive concept to those skilled in the art. Thus, the true spirit and scope of the inventive concept is not limited by the embodiment and examples described above but by the following claims.

What is claimed is:

1. An optical module for surface inspection, comprising:
a first light source unit including a first light source that produces a first light and a first beam splitter that changes the direction along which the first light propagates from the first light source,
the first light source unit oriented to illuminate an imaging plane, corresponding to a surface of a substrate to be inspected using the module, with the first light whose direction of propagation has been changed by the beam splitter;
a second light source unit that produces a second light polarized in a first direction, the second light source oriented to illuminate said imaging plane with the second light;
a direction of polarization changing unit oriented to receive the second light reflected from said imaging plane when the field is occupied by the surface of the substrate to be inspected,
wherein the direction of polarization changing unit comprises optics which convert the second light received into third light polarized in a second direction, perpendicular to the first direction, and propagating in a direction back to said imaging plane; and
a detection unit operative to detect captured light and positioned in the module to capture fourth light that is a product of the first light reflecting from said imaging plane when the imaging plane is occupied by the surface of the substrate to be inspected, fifth light that is a product of the second light scattered from said imaging plane when the imaging plane is occupied by the surface of the substrate to be inspected, and sixth light that is a product of the third light scattered from said imaging plane when the imaging plane is occupied by the surface of the substrate to be inspected.

2. The optical module of claim 1, wherein the first beam splitter is disposed along an optical axis of the module between said field and the detection unit, whereby the fourth light, the fifth light, and the sixth light are incident on the first beam splitter.

3. The optical module of claim 1, wherein the direction of polarization changing unit includes a quarter wave plate and a mirror.

4. The optical module of claim 3, wherein the mirror is a concave mirror.

5. The optical module of claim 1, wherein:
the first beam splitter is a dichroic beam splitter, and
the transmittance of the first beam splitter for the fourth light is 50%, and the transmittance of the first beam splitter for the fifth light and the sixth light is 90% or more.

6. The optical module of claim 1, further comprising:
a second beam splitter disposed along the first optical axis between the first beam splitter and the detection unit, and
wherein the detection unit includes a first detector and a second detector.

7. The optical module of claim 6, wherein:
the second beam splitter is a polarizing beam splitter,
the polarizing beam splitter transmits the fifth light and reflects the sixth light, and the first detector is positioned to capture the fifth light, and the second detector is positioned to capture the sixth light.

8. The optical module of claim 6, wherein:
the second beam splitter is a dichroic beam splitter,
the dichroic beam splitter transmits the fifth light and the sixth light and reflects the fourth light, and
the first detector is positioned to capture the fifth light and the sixth light, and the second detector is positioned to capture the fourth light.

9. The optical module of claim 8, further comprising:
a polarizing beam splitter through which the fifth light and the sixth light passing through the second beam splitter pass,
wherein the polarizing beam splitter reflects the fifth light and transmits the sixth light.

10. The optical module of claim 6, wherein the first detector and the second detector each detect light in the visible spectrum and output signals representative of the detected light.

11. The optical module of claim 1, wherein:
the detection unit includes a single detector, and
the detector is positioned to capture the fourth light, the fifth light, and the sixth light.

12. The optical module of claim 1, wherein:
the second light source unit includes a second light source and a polarizing beam splitter,
the second light source is a laser light source, and the polarizing beam splitter transmits the second light and reflects the third light.

13. The optical module of claim 12, wherein:
the second light source unit further includes a beam dump, and
the beam dump absorbs the third light reflected from the imaging field when the field is occupied by the surface of the substrate to be inspected.

14. An optical module for surface inspection, comprising:
a first light source unit configured to illuminate first light to an inspected substrate and including a first light source generating the first light and a first dichroic beam splitter changing a path of the first light;
a second light source unit configured to illuminate second light to the inspected substrate; and
a detection unit configured to detect third light produced by reflecting the first light on the inspected substrate and fourth light produced by scattering the second light on the inspected substrate,
wherein the third light and the fourth light pass through the first dichroic beam splitter to reach the detection unit, and
the transmittance of the first dichroic beam splitter for the third light is 50%, and the transmittance of the first dichroic beam splitter for the fourth light is 90% or more.

15. The optical module of claim 14, further comprising:
a second dichroic beam splitter through which the third light and the fourth light pass before being detected by the detection unit,
wherein the second dichroic beam splitter reflects all the third light and transmits the fourth light.

16. An optical module for use in inspecting the surface of a substrate, the module comprising:
a first light source unit that outputs first light along a first optical axis of the module, the first light source unit including a first light source, and a beam splitter oriented to reflect light produced by the first light source along the first optical axis of the module;
a second light source unit that outputs light polarized in a first direction along a second optical axis that intersects the first optical axis at an imaging plane and is oblique with respect to the first optical axis; and
a detection unit including a light detector,
wherein the beam splitter is disposed along the first optical axis between the imaging plane and the light detector, and the beam splitter has a transmittance with respect to the first light and the polarized second light,
whereby the light detector captures light that is a product of the first light reflecting from a surface of a substrate oriented substantially perpendicular to the first optical axis and lying in the imaging plane, and captures light that is a product of the polarized second light scattered from the surface of the substrate.

17. The optical module of claim 16, wherein the beam splitter is a dichroic mirrored prism.

18. The optical module of claim 16, wherein the second light source unit is disposed on one side of the first optical axis, and further comprising:
an optical unit disposed on the other side of the first optical axis, the optical unit including optics that changes the direction of polarization of light incident on the optical unit and outputs the light whose direction of polarization has been changed along a third optical axis oblique to said first optical axis and intersecting the imaging plane.

19. The optical module of claim 18, wherein the optics of the optical unit comprise a quarter wave plate and a concave mirror.

20. Optical apparatus comprising the optical module as claimed in claim 16, a substrate support over which the optical module is disposed, and a signal processor operatively connected to the detection unit.

* * * * *